United States Patent [19]

Würsch

[11] Patent Number: 4,999,197

[45] Date of Patent: Mar. 12, 1991

[54] COMPOSITIONS DERIVED FROM CAROB POD PROCESS FOR PREPARING

[75] Inventor: Pierre Würsch, La Tour-de-Peilz, Switzerland

[73] Assignee: Nestac S.A., Vevey, Switzerland

[21] Appl. No.: 892,939

[22] Filed: Aug. 4, 1986

[30] Foreign Application Priority Data

Aug. 30, 1985 [EP] European Pat. Off. ........ 85110944.7

[51] Int. Cl.$^5$ ............................................. A61K 35/78
[52] U.S. Cl. ................................................. 424/195.1
[58] Field of Search ..................................... 424/195.1

[56] References Cited

U.S. PATENT DOCUMENTS

| | | | |
|---|---|---|---|
| 438,020 | 10/1890 | Rambousek | 424/195.1 |
| 2,522,306 | 9/1950 | Serrallach | 424/195.1 |
| 4,244,982 | 1/1981 | Menzi et al. | 426/568 |
| 4,292,337 | 9/1981 | Andersen | 426/573 |

OTHER PUBLICATIONS

Würsch, et al., "The Tannin Granules from Ripe Carob Pod", Lebenson-Wiss. Technol, 1984, 17(6), 351-4 (Eng.).
Josylu, et al., "Leucoanthocyanins and Related Phenolic Compounds of Carob Pods (*Ceratonia siliqua*)", J. Sci. Fd. Agric., 19, pp. 540-550, 1968.
Tamir, et al., "Carob Tannins-Growth Depression and Levels of Insoluble Nitrogen in the Digestive Tract of Rats", J. Nutrition, 100, pp. 573-580, 1970.
Würsch, "Influence of Tannin-Rich Carob Pod Fiber on the Cholesterol Metabolism in the Rat", J. Nutrition, 109, pp. 685-692, (1979).
Hawley, *The Condensed Chemical Dictionary*, Tenth Edition, pp. 479, 778, (1981).
Weissberger, *Technique of Organic Chemistry, vol. III, Second Edition, Part I, Separation and Purification*, pp. 817-839, (1956).
Wuersch, et al., Chem Abs., 102, 77461h, (1985).

*Primary Examiner*—John W. Rollins
*Attorney, Agent, or Firm*—Vogt & O'Donnell

[57] ABSTRACT

Compositions are prepared from carob pods which are particularly useful for the treatment of diarrhoea. To prepare the compositions, ripe carob pods are treated with an aqueous medium for extracting sugars and water-soluble tannins, the residue is separated from the liquid phase containing the extracted materials and then the residue is dried under conditions which avoid thermal denaturing of the water-insoluble tannins contained in the residue. The compositions contain water-insoluble native tannins in an amount of at least 20% by weight, based upon dry matter, expressed as total polyphenols and have a ratio of water-soluble to water-insoluble tannins of below 0.37 as determined in water at 37° C. The dried residue is ground to a particle size up to 200 μm in diameter and may be formulated with food-acceptable additives.

3 Claims, No Drawings

COMPOSITIONS DERIVED FROM CAROB POD PROCESS FOR PREPARING

BACKGROUND OF THE INVENTION

This invention relates to a dietetic product with depurative and anti-diarrhoeic activity.

Diarrhoeic illnesses, which are very common, constitute a very important factor in infantile and even adult mortality. Diarrhoea consists of a very frequent and very rapid passage of unformed stools and is characterized by the elimination of an excess of water in the stools, leading progressively to dehydration. This phenomenon appears to be caused by malabsorption, by excessive secretion or even by a deficiency in intestinal motility; and these deficiencies may be concomitant. Although diarrhoea has several causes, it is accepted that the principal origin is the presence of bacterial or viral toxins in the intestinal tract.

In simple terms, diarrhoea is at present treated with products which absorb water, toxins, viruses or bacteria by a physical phenomenon or with medicaments which stimulate absorption, inhibit secretion or modify intestinal motility or even antibiotics or even with rehydration solutions containing water and mineral salts which are administered orally or intravenously.

The medicaments have the disadvantage that they are not always effective and produce side effects. Products which absorb water, for example gums, pectins, methyl cellulose, or carrots, may modify the frequency and consistency of the stools, but do not reduce the losses of water and electrolytes. Although rehydration solutions enable these losses to be compensated, they attenuate the effects of the diarrhoea instead of attacking its causes. Products capable of absorbing toxins, viruses and bacteria, for example calcium carbonate, hydrated aluminium silicate, bismuth salts, pectins, or active carbon, are very popular, but it is not certain whether they are really effective. Ion exchange resins, which additionally have the property of fixing the bile salts, appear to be effective, but also produce side effects and have to be used in high doses.

A dietetic composition containing from 60 to 80% roasted carob flour is commercially available (AROBON). Although this product gives good results in the treatment of diarrhoea without producing side effects, it has the disadvantage of necessitating relatively high doses, of the order of 20–40 g/day for young children, which presents problems of administration.

SUMMARY OF THE INVENTION

The present invention provides a dietetic product which is active in the treatment of diarrhoea without having any of the disadvantages mentioned above.

The dietetic product according to the invention is characterized in that it comprises as an active principle a carob, flour containing at least 20% by weight, based on dry matter, of native tannins, expressed as total polyphenols, of which the ratio by weight of soluble tannins to insoluble tannins is below 0.37, solubility being determined in water at 37° C.

The present invention also relates to a process for the preparation of carob flour characterized in that ripe carob pods are treated with an aqueous medium to extract most of the sugars and water-soluble tannins, the residue is separated, dried under conditions which avoid thermal denaturing of the water-in-soluble tannins present in the residue, i.e., at a temperature not exceeding 100° C., and then ground into particles smaller than or equal to 200 μm in diameter.

DETAILED DESCRIPTION OF THE INVENTION

In the context of the invention, native tannins are understood to be tannins which have not been denatured by a heat or chemical treatment. For example, when non-desugared or partially desugared carob pods (*Ceratonia siliqua*) are roasted, a Maillard reaction takes place which destroys the structure of the tannins, as reflected in the fact that the crystals characteristic of condensed carob tannins are no longer visible under a microscope. Similarly, if, for example, carob is treated with acids, the tannins are converted into phlobaphenes by polymerization.

In ripe carob, the majority of tannins are present in condensed form, i.e., in the form of polymers consisting of sub-units of 3-flavanol and gallic esters thereof. These tannins are insoluble in cold or tepid water and particularly at body temperature, i.e., at 37° C. The result of this is that they arrive in the intestine without having been degraded by gastric acid or inactivated by proteins. Accordingly, they are able to perform their depurative and antiseptic function without intervening in the physiological processes.

The tannin content may be evaluated by determining the total polyphenols, for example by applying a modified version of the colorimetric method of Folin-Denis, "Tannin" in Official Methods of Analysis (1980), W. Horwitz, ed., Association of Official Analytical Chemists, Washington D.C. This modified method comprises initially determining the soluble tannins, extracted with water at 37° C. while stirring moderately for 15 mins., in the supernatant liquid obtained after decantation. This is followed by determination of the condensed tannins which are insoluble in water at 37° C. and which are extracted from the solid phase with dimethyl formamide at 120° C. over a period of 4 h with intermittent stirring every 20 mins. The tannins may also be determined by gravimetry using the method described by L. Vuataz, H. Branderberger and R. Egli in J. Chromatogr. (1959), Vol. 2, pp. 173–187.

The carob flour is preferably enriched with tannins in relation to the ripe carob pod. Advantageously, it contains from 30 to 90% by weight, based on dry matter, of tannins expressed as total polyphenols. Among these tannins, the solubles advantageously represent less than 10% and preferably less than 6% by weight, for example approximately 4% by weight. The ratio by weight of soluble tannins to insoluble tannins is thus preferably from 0.04 to 0.1.

The dietetic product according to the invention may be presented in any form suitable for oral administration. Thus, it may be formulated as a powder for dispersion in an aqueous medium, for example water, milk, a fruit juice, or an isotonic beverage. In addition to carob flour, a powder such as this will advantageously contain permitted food additives, for example effervescent agents, for example a mixture of acid and carbonate, wetting agents, for example lecithin, flavourings, rehydration salts, or peptides emanating, for example, from hydrolyzed proteins. It may also contain sugars, advantageously maltodextrin, dextrose or preferably sucrose, for example, in the quantity necessary to standardize the percentage by weight of tannins, expressed as total polyphenols, of the preparation to a predetermined value, preferably of the order of 22% by weight.

Alternatively, the dietetic product may be presented in the form of optionally effervescent granulates, tablets or dragees for chewing or dissolving prepared from the flour by standard methods.

Finally, the dietetic product may be presented as a food, advantageously a dessert, for example a cream, a jelly or a baked custard in which the carob flour is incorporated.

The quantity administered will of course depend upon the age of the patient (infant, child or adult), upon the nature and gravity of the diarrhoea to be treated and upon the nature of the treatment itself (preventive or curative). For instance, a dose comprising 1-2 g carob flour/kg body weight/day and preferably 1 g/kg/day up to 10 kg body weight and up to 20 g/day beyond 10 kg body weight enables the diarrhoea to be treated in 8 to 10 days. The flour may be dispersed in an aqueous medium in a quantity of from 1 to 3% by weight.

The flour may be packed, preferably in an inert atmosphere, for example in 100 g boxes with a measuring spoon or in sachets of 5-10 g which are impermeable to air, light and moisture.

The above carob flour shows bactericidal activity on enteropathogenic *Staphylococcus aureus* and *E. coli* and bacteriostatic activity on *E. coli*. Its inhibiting effect is probably due to the mechanical adsorption of the bacteria onto the granules of tannins which it contains and to the progressive release of the soluble tannins from those granules. It has also been found that the granules of tannins in question adsorb the enterotoxin of cholera and the thermolabile enterotoxin of *E. coli* and that they inactivate the enteroviruses. In the doses in which they are taken, these tannins do not affect the normal process of digestion despite the antinutritional activity which they are known to show through inhibition of the digestive enzymes. They have a detoxificating effect and a delayed action and are not absorbed in contrast to the antibiotics normally prescribed.

The ripe carob pods used as starting material are characterized by a percentage sugar content which has reached the maximum through ripening, i.e., approximately 50% by weight, of which approximately 40% by weight is sucrose, and by a moisture content of less than 20% by weight. They are preferably crushed into fragments smaller than 1.5 cm in diameter, if necessary after having been frozen. The carob without the seeds thus has the following standard composition:

|  | % by weight of dry matter |
|---|---|
| Soluble carbohydrates | 49 |
| Soluble polyphenols | 1.2 |
| Insoluble tannins (determined by gravimetry) | 19.8 |
| incl. polyphenols | (11) |
| Pectin, hemicellulose-lignocellulose | 24.5 |
| Proteins (N × 6.25) | 3 |
| Ash | 2.5 |

In a first continuous embodiment of the process, which is preferred, the carob is ground in the presence of cold water, for example at 15° to 20° C., for example in a colloid mill. The quantity of water added is preferably from 5 to 15 times the quantity of carob. After separation of the liquid phase, for example in a decanter, the desugared carob is collected.

The desugared carob is preferably heat-treated, for example by addition of an equivalent quantity by weight of hot water, after which the dispersion is pasteurized, for example by the direct injection of steam at 95°-98° C. for 30 s to 10 mins. This heat treatment has the advantage of removing most of the microorganisms from the dispersion before it is subsequently ground.

The pasteurized dispersion is then ground, preferably first in a toothed mill and then in an edge mill at a temperature not exceeding about 90° C. The dispersion is then dried, preferably by spraying into a tower. Drying takes place under conditions which avoid thermal denaturing of the tannins, i.e., at a temperature not exceeding 100° C. and preferably at a temperature of 90° C. at the level of the product.

Finally, the powder obtained is dry-ground, for example in a pinned-disc mill, to give a flour of which the particles have a diameter of less than or equal to 200 μm, advantageously from 10 to 200 μm and preferably of the order of 100 μm, which ensures that no unpleasant granularity can be detected in the dietetic product containing the flour and avoids rapid sedimentation of the particles, for example in a beverage.

In a second embodiment of the process, which is carried out in batches, the crushed carob, preferably in the form of particles 0.8 to 5 mm in diameter, is introduced into hot water, preferably at 60° to 98° C. Columns may be filled with the crushed carob and water subsequently passed through the columns thus filled or, alternatively, the crushed carob may be suspended in water in tanks and the suspension stirred. The solid phase is then collected, for example by gravity or by decantation, and dried in hot air. For example, the moist residue may be placed on shelves in a dryer, in which preferably a partial vacuum and a temperature of from 60° to 70° C. prevail, and left there for 24 to 72 h. Finally, the dried material is ground, for example in a pinned-disc mill, to give particles from 10 to 200 μm in diameter and preferably around 100 μm in diameter.

In a variant of the embodiments described above, which enables the flour to be enriched with tannins, the dispersion or the residue may be dried, for example by freeze drying, converted into granules, for example by means of a granulation plate, and the granules thus formed crushed, for example in an edge mill or in a cylinder mill, and most of the fines eliminated, for example by elutriation in a stream of hot air.

The particles obtained preferably have diameters of from 10 to 200 μm. Examples

The invention is illustrated by the following Examples in which the percentages represent percentages by weight, unless otherwise indicated.

EXAMPLE 1

1.7 kg/min of ripe deseeded carob pods crushed into particles having an average diameter of 2 cm and having a dry matter content of 95% are continuously introduced into a colloid mill in the presence of 21 1/min running water at 18° C., the dispersion being removed through a sieve having a mesh width of 1 mm. After a dwell time of 6 mins., the dispersion is introduced into a decanter in which the liquid phase is separated and the solid phase containing 18% of fibres, expressed as dry matter, is collected.

After the solid phase has been mixed with as much running water at 95° C., the dispersion is pasteurized by direct injection of steam at 95°-97° C. for 30 s and then ground at 85° C. first in a toothed mill and then in an edge mill. The ground dispersion is then dried by spraying into a tower at 175 1/h, the entry air temperature being from 165° to 170° C. and the exit air temperature from 96 to 98° C. Under these conditions, the temperature at the level of the product does not exceed 90° C. Finally, the powder is dry-ground in a pinned-disc mill rotating at 9000 r.p.m.

The particles obtained have a dry matter content of 3%. 50% pass through a 75 μm mesh screen and 100% through a 200 μm mesh screen.

The flour has the following composition, expressed as dry matter:

|  | % |
| --- | --- |
| Soluble carbohydrates | 19.3 |
| Tannins (gravimetry) | 47.4 |
| incl. polyphenols | (27) |
| Fibres | 25.7 |
| Proteins | 4.8 |
| Ash | 2.8 |

The ratio of soluble tannins to insoluble tannins is 0.23:1.

EXAMPLE 2

127 kg of deseeded crushed ripe carob pods having a dry matter content of 89% are frozen at −40° C., size-reduced in a cutter with an opening of 3 mm and the fines subsequently eliminated through a 0.8 mm mesh screen. The remaining 108 kg are introduced into columns. After the particles have been swollen in deionized water, deionized water at 70° C. is passed through the columns at a rate of 180 1/h. After the columns have been drained by gravity, 210 kg of solid particles having a dry matter content of 19% are collected. The wet particles are placed on shelves in an air dryer and dried for 48 h at an air temperature of 80° C. and under a pressure of 60 mb. 42.5 kg of dried material having a dry matter content of 89.5% are thus obtained. Finally, this material is ground at a rate of 40 kg/h in a pinned-disc mill rotating at 12,000 r.p.m. which gives 40 kg of flour of which the particles have a dry matter content of 92% and an average diameter of 100 μm.

The flour has the following composition, expressed as dry matter:

|  | % |
| --- | --- |
| Soluble carbohydrates | 22.5 |
| Tannins (gravimetry) | 36.2 |
| incl. polyphenols | (22.6) |
| Fibres | 34.9 |
| Proteins | 4.6 |
| Ash | 1.8 |

The ratio of soluble tannins to insoluble tannins is 0.06:1.

EXAMPLE 3

29 kg of ripe carob pods which have been stored for at least 6 months, deseeded, crushed and ground into particles having an average diameter of 5 mm are treated with 100 kg deionized water at 98° C. in a tank with stirring for a period of 10 minutes. The dispersion is then centrifuged, 34.5 kg of residue are collected and are then washed for 10 mins. at 15° C. with 100 kg deionized water. After the dispersion has been re-centrifuged, 27.2 kg of residue are collected and are then dried by freeze drying. After granulation into particles having an average diameter of 3 mm on a granulation plate, the particles are crushed in a cylinder mill and the fibres are eliminated by a stream of hot air. Final grinding in a micronizer gives a flour which is enriched with insoluble tannins in relation to the starting carob and of which the particles have an average diameter of 25 μm.

The flour has the following composition, expressed as dry matter:

|  | % |
| --- | --- |
| Soluble carbohydrates | — |
| Tannins (gravimetry) | 71.7 |
| incl. polyphenols | (41.9) |
| Fibres | 22.6 |
| Proteins and ash | 5.7 |

The ratio of the soluble tannins to the insoluble tannins is 0.04:1.

EXAMPLE 4

82% carob flour prepared in accordance with Example 1 are dry-mixed for 30 mins. with 17.9% finely ground sucrose containing 3% soya lecithin and 0.1% vanillin and the resulting mixture is ground in a mill having a 0.8 mm mesh sieve. The powder is then packed together with a measuring spoon in 160 g boxes which are impermeable to light, air and moisture.

EXAMPLE 5

Effervescent granulates

Premix I 80 g gelatin, 2 kg carob flour prepared in accordance with Example 1 and 160 g maltodextrin having a dextrose equivalent of 5% are dry-mixed.

4 liters cold deionized water are added to this mixture in a kneader and the whole is homogeneously mixed. The paste is then dried for 12 h at 40°-50° C. in a shelf dryer.

Premix II

An effervescent premix containing 25% citric acid, 52.3% sodium bicarbonate and 22.7% tartaric acid is prepared, after which 21.6 g powder-form vegetable wax, 4.8 g magnesium stearate and 50.4 g orange flavouring are added to 75.2 g of this premix.

Premixes I and II are thoroughly mixed and then ground into granulates having an average diameter of 1.5 mm.

EXAMPLE 6

Effervescent tablets

Effervescent tablets weighing 0.65 g for a diameter of 1 cm and a thickness of 7.2 mm are prepared from the granulates obtained in accordance with Example 5 by compressing the granulates in a cylindrical chamber 1 cm in diameter and 16 mm deep.

EXAMPLE 7

Chewing tablets

Chewing tablets are prepared from the following ingredients:

|  | % |
| --- | --- |
| Carob flour of Example 1 | 81.4 |
| Corn protein | 7.1 |
| Edible fat | 3.4 |

-continued

| | % |
|---|---|
| Mint flavouring | 1.5 |
| Maltodextrin | 6.2 |
| Calcium stearate | 0.4 |

The various ingredients are dry-mixed and then compressed as in Example 6.

EXAMPLE 8

Chewing granulates

After dry-mixing of the following ingredients:

| | % |
|---|---|
| Carob flour of Example 1 | 80 |
| Malt extract | 10 |
| Cocoa butter | 10 | granulates are prepared using a compactor comprising hollow toothed wheels drilled with holes 2-3 mm in diameter. Scrapers placed inside the wheels cut the strands issuing from the holes into granulates which are then coated with a film of gum arabic and sprayed with a flavoured sugar syrup.

EXAMPLE 9

Flavoured milk

A flavoured milk is prepared by mixing 15 g wholemilk powder containing 50% sucrose with 6 g of the flour of Example 1 and traces of strawberry flavouring.

A beverage is obtained by diluting this mixture in 100 ml water.

EXAMPLE 10

Cream

A chocolate-flavoured cream is prepared from 50 g of a powder-form chocolate cream mix to which 12 g of the carob flour of Example 1 are added, the whole then being diluted in 100 ml cold milk. The cream obtained is homogeneous and the presence of the carob flour is not noticeable.

EXAMPLE 11

Powder for oral rehydration

The following ingredients are dry-mixed in the quantities indicated:

| Potassium chloride | 1.5 g |
|---|---|
| Sodium chloride | 3.5 g |
| Sodium hydrogen carbonate | 2.5 g |
| Glucose monohydrate | 20 g |
| Flour of Example 1 | 10-15 g |

At the moment of use, this mixture is diluted in 1 liter running water preferably sterilized beforehand. The volume of liquid to be ingested for children is 50-100 ml/kg body weight/4 h and up to 750 ml/h for adults, the quantity of flour ingested per day not exceeding 20 g.

EXAMPLE 12

The effect of the flour obtained in accordance with Example 1 on acute diarrhoea (6-12 stools/day) in children caused predominantly by E. coli was studied. 33 children aged between 5 and 30 months were given 1 g carob flour per kg body weight mixed with porridge. In 28 cases (85%), the diarrhoea was stopped in 48-72 h.

Another group of 31 children aged between 1 and 12 months suffering from acute diarrhoea (more than 5 stools/day) was given 5 g per kg body weight and at most 40 g/day of commercial roasted carob flour (AROBON) in a milk in a quantity of 5%. 26 cases (84%) were cured in 7 days.

Another comparison group treated with an antibiotic, namely chloramphenicol, showed 64% recovery after 7 days.

It can thus be seen that the carob flour prepared in accordance with the invention is more active in a 5 times smaller dose than the roasted carob flour and a widely prescribed antibiotic without having any of the disadvantages of the antibiotic (side effects, deterioration of the intestinal flora).

I claim:

1. A process for preparing a carob derived composition comprising grinding ripe carob pods in a cold water medium for extracting sugars and water-soluble tannins from the pods into the water medium to obtain a ratio of water-soluble tannins to water-insoluble tannins in a residue of the pods below 0.37, as determined in water at 37° C., separating the residue of the extracted pods from the water medium, forming an aqueous dispersion of the residue, pasteurizing the residue dispersion at 95° C. to 98° C. for from 30 secs to 10 mins, grinding the pasteurized dispersion at a temperature not exceeding about 90° C., spray-drying the ground pasteurized dispersion at a temperature not exceeding 100° C. and grinding the dried residue for obtaining particles having a size of up to 200 μm in diameter.

2. A process according to claim 1 wherein the cold water is at a temperature of from 15° C. to 20° C.

3. A process according to claim 1 wherein the dispersion is pasteurized with steam.

* * * * *

UNITED STATES PATENT AND TRADEMARK OFFICE
CERTIFICATE OF CORRECTION

PATENT NO. : 4,999,197
DATED : March 12, 1991
INVENTOR(S) : Pierre WURSCH It is certified that error appears in the above-identified patent and that said Letters Patent is hereby corrected as shown below:

In the title, "COMPOSITIONS DERIVED FROM CAROB POD PROCESS FOR PREPARING" should be --PROCESS FOR PREPARING COMPOSITIONS DERIVED FROM CAROB POD--.

Signed and Sealed this

Eighteenth Day of August, 1992

Attest:

DOUGLAS B. COMER

*Attesting Officer*    *Acting Commissioner of Patents and Trademarks*